United States Patent [19]
Thompson et al.

[11] Patent Number: 5,480,629
[45] Date of Patent: Jan. 2, 1996

[54] CATALYTIC PRODUCTION OF HYDROGEN PEROXIDE

[75] Inventors: Mark E. Thompson, Hamilton Square; Jonathan L. Snover, Mercerville; Vijay Joshi, Livingston, all of N.J.; Lori A. Vermeulen, Hurst, Ill.

[73] Assignee: The Trustees of Princeton University, Princeton, N.J.

[21] Appl. No.: 287,140

[22] Filed: Aug. 8, 1994

Related U.S. Application Data

[63] Continuation-in-part of Ser. No. 103,968, Aug. 9, 1993.
[51] Int. Cl.$^6$ ................................................. C01B 15/01
[52] U.S. Cl. .................................................. 423/584
[58] Field of Search ........................................ 423/584

[56] References Cited

U.S. PATENT DOCUMENTS

| | | | |
|---|---|---|---|
| 4,128,627 | 12/1978 | Dyer et al. | 423/584 |
| 4,336,240 | 6/1982 | Moseley et al. | 423/584 |
| 4,369,128 | 1/1983 | Moseley et al. | 423/584 |
| 4,711,772 | 12/1987 | Jacobson | 423/584 |

*Primary Examiner*—Wayne Langel
*Attorney, Agent, or Firm*—Mathews, Woodbridge & Collins

[57] ABSTRACT

A method for the production of hydrogen peroxide from a source of hydrogen and a source of oxygen in the presence of a catalyst comprising the formula:

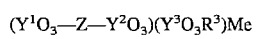

$Y^1$, $Y^2$ and $Y^3$ being phosphorus or arsenic; Z being a divalent group containing two conjugated cationic centers; $R^3$ being a capping group and Me being a trivalent or tetravalent metal.

20 Claims, 2 Drawing Sheets

FIG. 2
FIG. 3
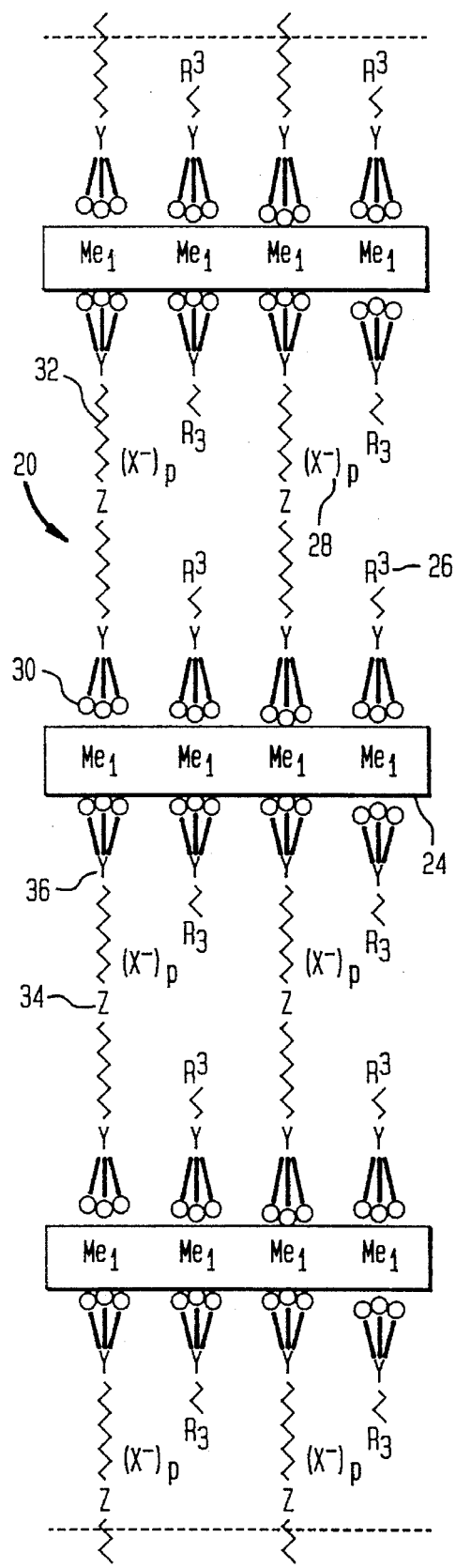
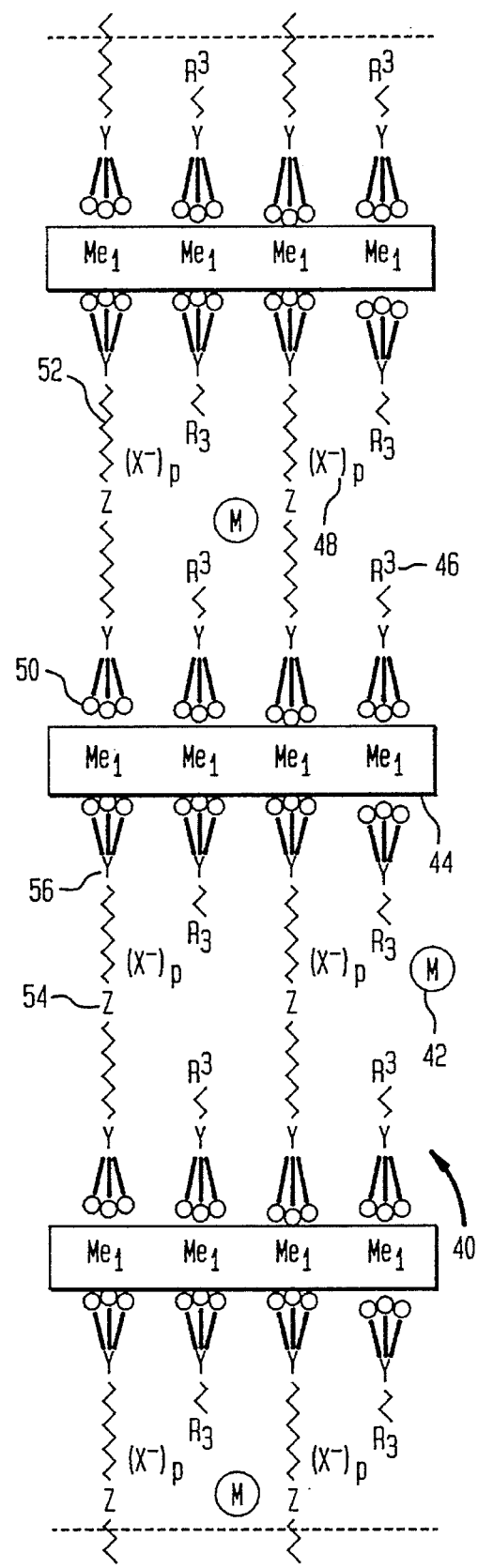

CATALYTIC PRODUCTION OF HYDROGEN PEROXIDE

This is a continuation-in-part of Ser. No. 08/103,968 filed Aug. 9, 1993, pending, the disclosure of which is incorporated here by reference.

TECHNICAL FIELD

The present invention pertains to stable electron acceptor compositions which have efficient and sustained photoinduced charge separation states.

BACKGROUND OF THE INVENTION

Solar energy can be used and stored by the efficient production of long-lived photo-induced charge separation—a state achieved in photosynthetic systems by the formation of a long-lived radical pair. A number of artificial systems have been reported that efficiently undergo photochemical charge transfer, unfortunately, the thermal back electron transfer often proceeds at an appreciable rate, limiting the utility of these systems. What is needed is a systems which has very efficient photoinduced charge transfer, and forms a charge-separated state which is long lived in air. The charge separation in these systems typically involves a redox reaction between a photoexcited donor and a suitable acceptor, resulting in the production of radical ion pairs illustrated by the formula:

$$D + h\nu \rightarrow D^* \quad (1a)$$

$$D^* + A \rightarrow A^- + D^+ \quad (1b)$$

$$D^+ + A^- \rightarrow D + A \quad (2)$$

The cation and anion generated in this way are better oxidants and reductants, respectively, than either of the neutral ground-state molecules. To harvest the light put into this system, the oxidizing and reducing power of the photogenerated species must be used before the electrons are transferred back (equation 2) generating the starting materials. It is desirable to control this photochemically unproductive thermal fast back electron transfer reaction. One method has been to incorporate the donors and acceptors into solid matrices.

Compounds which can carry out reduction reactions, using hydrogen gas as their reducing equivalents, are useful as catalysts for the conversion of mixtures of hydrogen and oxygen to hydrogen peroxide. Hydrogen peroxide is a very large volume chemical. The United States annual production is greater than 500 million lbs. Several processes have been patented for the production of hydrogen peroxide, which depend on the two following reactions. The goal is to promote reaction (1) and retard reaction (2).

$$H_2 + O_2 \rightarrow H_2O_2 \quad (1)$$

$$H_2O_2 + H_2 \rightarrow 2\,H_2O \quad (2)$$

A number of catalysts for this conversion have been reported including both homogeneous and heterogeneous catalysts. The higher yielding homogenous catalysts, for example those disclosed in U.S. Pat. Nos. 4,800,075; 4,046,868; 4,668,499; 5,254,326; 5,194,067; 5,041,680; 5,039,508; 4,994,625; and 4,897,252, are limited by the difficult step of separating the hydrogen peroxide from the reaction mixture. The heterogenous catalysts allow easy isolation of the hydrogen peroxide but require high pressure and exhibit short catalytic lifetimes, such as the one disclosed in U.S. Pat. No. 4,832,938 ("the DuPont patent"). The DuPont catalyst system consists of colloidal metal particles bound to inert supports, such as silica, alumina and carbon. These materials are prepared by first generating an aqueous suspension of the desired metal colloid (with a set ratio of Pt to Pd) and then spray drying this solution onto the inert support. The resulting solid is heated in hydrogen to 200° C. to form the catalyst. Bromide or chloride promoters as well as phosphonic acids were added to the system. The role of the promoters and phosphonic acid are not well defined. All of the chemistry occurs at the colloid particle. The peroxide production reaction involves treating an aqueous suspension of the catalyst with high pressures of hydrogen and oxygen (1000–2000 psi). The hydrogen adds to the surface as does the oxygen. The problem with this system is that the same particles that are good at forming peroxide (equation 1) are good at converting peroxide to water (equation 2). A wide range of different ratios of Pt:Pd was investigated to develop the most active catalyst. There is no reported analytical data on the materials of the DuPont patent. The ratios are calculated based on what goes in the flask and not what comes out. They do not report any evidence as to whether the Pd and Pt are uniformly mixed in their colloidal particles or they form separate species on the surface of the support. What is needed is a heterogeneous catalyst with an improved yield.

The compositions of the present invention are capable of producing a sustained photoinduced charge separation state which renders the compositions useful in solar energy conversion and storage. In addition, the compositions permit reduction of various metal ions to produce the zero-valence metal in colloidal form entrapped in the matrices of the compositions. These latter matrices containing the zero-valence metal have a variety of uses such as in the decomposition of water to yield hydrogen gas and the sensing of oxygen. In addition, the zero-valence metal matrices can be used in catalysis, as for example in the production of hydrogen peroxide and the oligomerization of methane to form higher hydrocarbons.

SUMMARY OF THE INVENTION

The present invention provides multi-layered, pillared metal complexes having a plurality of parallel "pillars" where the "pillars" are divalent electron acceptor moieties with a phosphonate or arsenate at each end. Each layer of parallel pillars is separated by a perpendicular layer of group (IVA), (IVB), (IIIA) or (IIIB) metal; and where particles of at least one Group VIII metal at zero valence are entrapped within each layer of the complexes. The complexes can incorporate "stalactites" and "stalagmites" of capped arsonato or phosphonato ligands interspersed with the pillars providing a series of interstices about each electron accepting group. The complexes are useful for the conversion and storage of solar energy and as catalysts for the production of hydrogen peroxide from oxygen and hydrogen sources.

BRIEF DESCRIPTION OF THE DRAWINGS

FIG. 2 is a schematic view of a solid composition according to the present invention.

FIG. 3 is a schematic view of a solid of the present invention incorporating metal particles according to the present invention.

DESCRIPTION OF THE PREFERRED EMBODIMENT

Figure 1:
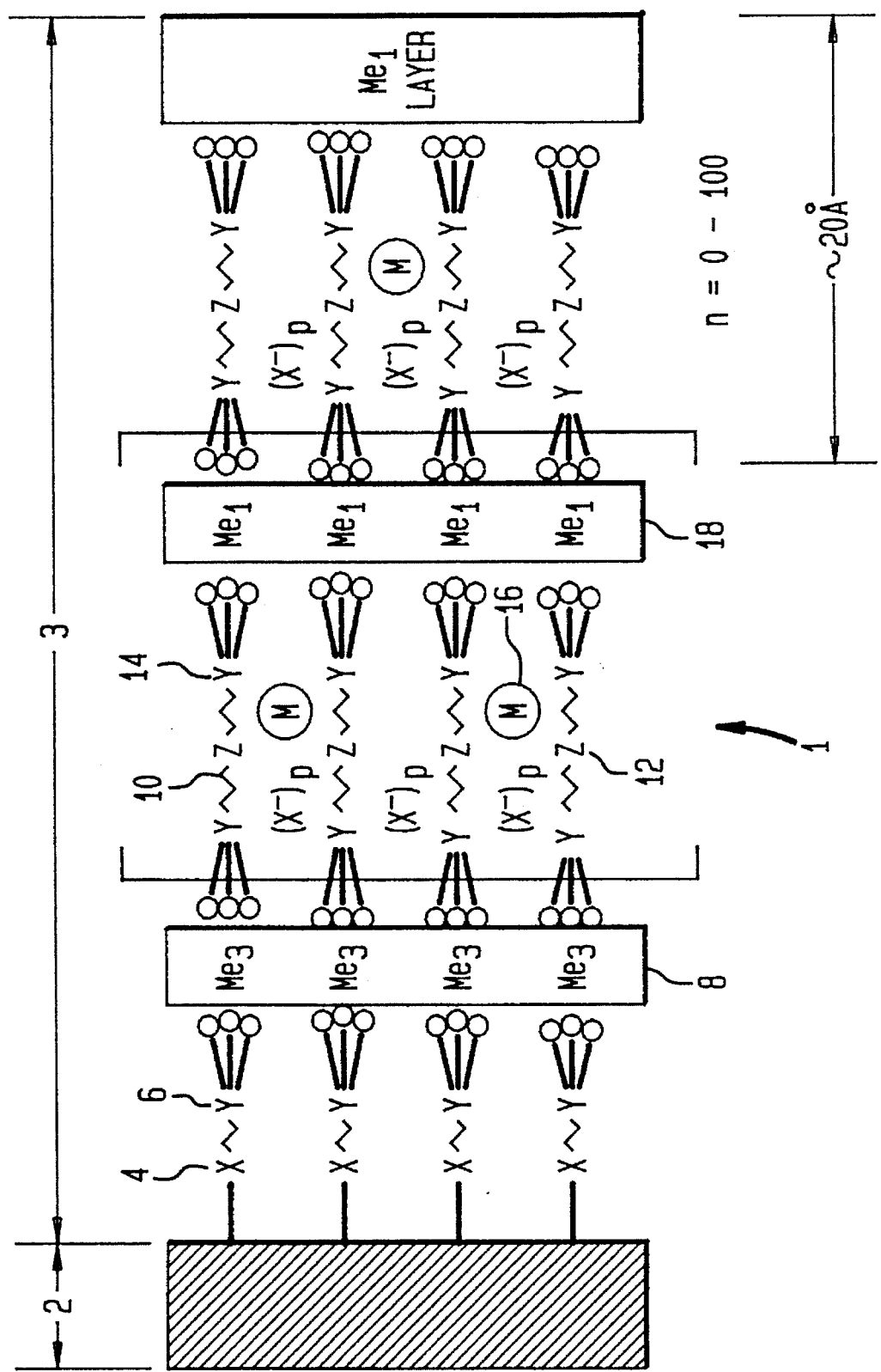
FIG. 1 is a schematic view of the highly ordered structure of a substrate and film according to the present invention.

In particular, the invention relates in a first embodiment to a composite composition in which a film is disposed on a supporting substrate. The film is composed of a plurality of pillared metal complexes, each of the formula:

$$-O-L-[(Y^1O_3-Z-Y^2O_3)\ Me^1]_k \cdot k^* p(X^{2/p-}) \qquad \text{I.}$$

in which:

L is a divalent linking group;

each of $Y^1$ and $Y^2$, independently of the other, is phosphorus or arsenic;

Z is a divalent group which reversibly forms a stable reduced form and contains two conjugated cationic centers which together have a negative $E°_{red}$ value;

$Me^1$ is a trivalent or tetravalent metal of Group III, IVA, or IVB having an atomic number of at least 21 or a lanthanide;

X is anion;

k has a value of from 1 to about 100; and p has a value of 1, 2 or 3.

$Me^1$ can be, for example, a group IVA metal having an atomic number of at least 21 such as germanium, tin, or lead, a group IVB metal such as titanium, zirconium, or hafnium, a group IIIA metal having an atomic number of at least 21 such as gallium, indium, or thallium, a group IIIB metal such as scandium, yttrium, or a lanthanide as for example lanthanum, cerium, praseodymium, etc. Of these, titanium, zirconium, hafnium, germanium, tin, and lead are preferred with zirconium being particularly useful.

Each of $Y^1$ and $Y^2$ is phosphorus or arsenic, preferably phosphorus, each of $Y^1O_3$ and $Y^2O_3$ thus being a phosphonato or arsonato group.

The group Z is divalent, being bound to the phosphorus or arsenic atom of the phosphonato or arsonato group defined by $Y^1O_3$ and $Y^2O_3$. In practice, the precise structure of the group Z is of lesser importance than its electronic properties. Firstly, it must containing two conjugated cationic centers which together have a negative $E°_{red}$ value; i.e., a reduction potential below that of hydrogen. Secondly, Z must be capable of existing both in a stable reduced form and reversibly in a stable oxidized form. The two conjugated cationic centers can be for example tetravalent nitrogen atoms which are conjugated ring members in an aromatic ring system.

In one embodiment, each tetravalent nitrogen atom is a ring member in a separate aromatic ring system and two such ring systems, which can be of the same or different structure, are joined to one another directly through a covalent bond. Each such aromatic ring system can be a monocycle such as pyridine, pyrazine, or pyrimidine. Alternatively, each aromatic ring system can be a fused polycycle in which a pyridine, pyrazine, or pyrimidine ring is fused to one or more benzo or naphtho ring system, as for example quinolinium, isoqunoinolinium, phenanthridine, acridine, benz[h]isoquinoline, and the like.

The two aromatic ring systems, which can be of the same or different structure, alternatively can be linked through a divalent conjugated system as for example diazo (—N=N—), imino (—CH=N—), vinylene, buta-1,3-diene-1,4-diyl, phenylene, biphenylene, and the like.

In a further embodiment, the two conjugated cationic centers can be in a single aromatic system such as phenanthroline, 1,10-diazaanthrene, and phenazine.

Typical dicationic structures suitable as Z thus include 2,2-bipyridinium, 3,3-bipyridinium, 4,4-bipyridinium, 2,2-bipyrazinium, 4,4-biquinolinium, 4,4-biisoquninolinium, 4-[2-(4-pyridinium)vinyl]pyridinium, and 4-[4-(4-pyridinium)phenyl]pyridinium.

The aromatic systems in which the two conjugated cationic centers are located can be unsubstituted or substituted, as for example with alkyl of 1 to 6 carbon atoms or alkoxy of 1 to 6 carbon atoms. Such substitution can be inert or can have an effect on the reduction potentials of the cationic centers sterically or through induction.

While the two cationic centers must be linked through conjugation, the entire system comprised by Z need not be conjugated. Thus Z can be joined to each of $Y^1O_3$ and $Y^2O_3$ through a conjugated or non-conjugated bridge. Hence one highly desirable structure for Z is characterized by the structure:

$$-(R^1)_n-Z'-(R^2)_m- \qquad \text{II.}$$

in which Z' is a divalent aromatic group containing at least two conjugated tetravalent nitrogen atoms; each of n and m, independently of the other, has a value of 0 or 1; and each of $R^1$ and $R^2$, independently of the other, is a divalent aliphatic or aromatic hydrocarbon group. Typically each of n and m will be 1 and each of $R^1$ and $R^2$, independently of the other, will be a straight or branched divalent alkane chain of six or less carbon atoms, as for example methylene, ethano, trimethylene, propane-1,2-diyl, 2-methylpropan-1,2-diyl, butane-1,2-diyl, butane-1,3-diyl, tetramethylene, and the like.

The group X is an anionic group one or more of which (depending on the value of k and the charge of X) will balance the cationic charges of Z. The precise nature of X is relatively unimportant and X can be for example a halogen anion such as chloride, bromide, iodide, a pseudohalide, sulfate, sulfonate, nitrate, carbonate, carboxylate, etc.

The composition comprises a supporting substrate to which is bound a film comprising a molecular plurality of the complexes of Formula I. Thus each complex depicted by Formula I is bound to the substrate through the depicted univalent oxygen atom. There is a molecular plurality of —L—Zr—$Y^1O_3$—Z—$Y^2O_3H_2 \cdot 2X^-$ units on a given substrate, thereby producing a pillared structure. Each complex can contain one Z-containing unit, in which case k has a value of 1, but preferably k has a value in excess of 1 so that the unit —$(Y^1O_3-Z-Y^2O_3)Me^1$— becomes the monomer of the pillared polymeric complex in which k ranges from 2 to about 100, typically from about 5 to about 50.

Such films are prepared through sequential adsorption reactions analogously to those described by Rong et al., *Coordination Chemistry Reviews*, 97, 237 (1990). Thus the substrate, which typically is hydroxy terminated, as for example metals (the surfaces of which invariably include the metal oxide), glass, silicas, gallium arsenide, and the like, is first derivatived with a hydroxy-reactive reagent which introduces the linking group L or components of that linking group. Typically the distal portion of L will terminate in, and thus eventually be bound to $Y^1O_3$ through, a metal atom $Me^3$ which is similar to $Me^1$ i.e., a trivalent or tetravalent metal of Group III, IVA, or IVB having an atomic number of at least 21, or a lanthanide.

Thus for example, the substrate can be treated with a compound of the formula:

$$X''-R^1-Z-Y^3O_3H_2 \cdot 2X' \qquad \text{III.}$$

in which $R^1$ and Z are as herein defined; $Y^3$ is phosphorus or arsenic; X' is an anion analogous to X (X' can be, but need not necessarily be, the same anion as will appear in the final complex) and X" is a reactive halogen such as chloro or bromo. Thereby produced is the intermediate:

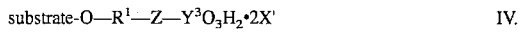

substrate-O—R$^1$—Z—Y$^3$O$_3$H$_2$•2X'   IV.

The foregoing reactions can be conducted in two stages, first by treating the substrate with a compound of the formula X"—R$^1$—Z•2X' and then treating the product with a phosphoryl halide such as phosphoryl chloride or phosphoryl bromide or a corresponding arsonyl halide.

In either aspect of this embodiment, the linking group produced is similar to the repeating unit insofar as it contains —Z—Y$^3$O$_3$.

Alternatively, the linking group can be dissimilar to the repeating unit. Thus the substrate can be treated a silane such as an aminoalkyltrialkoxysilane as for example 3-aminopropyltriethoxysilane and this derivatived substrate then treated with a phosphoryl halide such as phosphoryl chloride or phosphoryl bromide or a corresponding arsonyl halide to produce:

substrate-O—alkyl—Y$^3$O$_3$H$_2$.   V.

In either case, the intermediate having a surface rich in phosphonate or arsonate groups then is treated with a reagent providing Me$^3$ ions, e.g., zirconyl chloride. The metal ions bind to the phosphonate groups, in turn producing an intermediate having a metal rich surface and characterized as "substrate-L'" in which L' corresponds to the linking group of Formula I (but terminates in Me$^3$).

The precise chemical composition of L, and thus L', is relatively unimportant since it need only provide a link which (i) on the one hand binds to hydroxy groups on the substrate and (ii) on the other presents a metal Me$^3$ for further complexing.

The substrate-L' with the linking group bound to it then is separated from the reagent providing Me$^3$ ions, washed with water, and treated with a solution of a bisphosphonic acid or bisarsonic acid of the formula:

H$_2$Y$^1$O$_3$—Z—Y$^2$O$_3$H$_2$•2X'   VI.

in which Y$^1$, Y$^2$, Z, and X' are as defined above. This reaction is complete within a few hours, as for example about 4 to 5 hours, and can be accelerated through the use of moderate heat, as for example from about 80° to about 100° C. The deposition of this layer can be readily monitored spectrophotometrically at wavelengths of from about 260 to about 285 nm. For consistency, generally the range of 280–285 nm is employed. One of the —Y$^1$O$_3$H$_2$ and —Y$^2$O$_3$H$_2$ groups binds to the zirconium rich surface, while the other remains uncoordinated, thereby now producing an intermediate having a surface rich in phosphonate or arsonate groups. This intermediate can be depicted as:

substrate-O—L—Zr—Y$^1$O$_3$—Z—Y$^2$O$_3$H$_2$•2X'   VII.

The substrate-O—L—Zr—Y$^1$O$_3$—Z—Y$^2$O$_3$H$_2$•2X' is removed from the solution of the bisphosphonic acid or bisarsonic acid, rinsed thoroughly, and then treated with a reagent providing Me$^1$ ions to produce a complex of Formula I in which k is 1.

The foregoing sequence of the last two synthetic steps, that is treatment with a bisphosphonic acid or bisarsonic acid followed by treatment with a reagent providing Me$^1$ ions, is repeated to produce complexes having higher k values. Absorbance, as for example at 280–285 nm, appears to increase linearly with the number of layers and provides a convenient method of monitoring the formation of multilaminar compositions.

The foregoing procedure is readily and preferably modified to entrap atoms of at least one Group VIII metal, as for example platinum, palladium, iron, cobalt, nickel, ruthenium, rhodium, osmium, or iridium, at zero valence within the complexes. Thus following treatment with a bisphosphonic acid or bisarsonic acid but before treatment with a reagent providing Me$^1$ ions, the sample is immersed in an aqueous solution of a soluble anionic salt of the Group VIII metal. After a short time, the metal anion exchanges with some of the chloride anions in the sample. The stoichiometrics of this exchange will depend upon the respective valences of the two anions. The platinum tetrachloride and platinum hexachloride anions, for example, each have a valence of −2 and if chloride were the starting anion, one anion of either of these metal anions would exchange for two chloride anions.

Following this exchange, treatment with a reagent providing Me$^1$ ions then is performed as described above. As above, these reactions are repeated until the desired k value is attained. The composite is then simply exposed to hydrogen gas which reduces the metal anion to produce the metal in a zero valence state and colloidal form within the matrix of the composite. As noted previously, such materials are highly effective as catalysts in the production of hydrogen peroxide, the oligomerization of methane to form higher hydrocarbons, the decomposition of water to yield hydrogen gas, and the sensing of oxygen. The compositions also can be utilized to reduce various organic substrates.

It is possible to utilize more than one Group VIII metal in any sample, either using soluble salts of different Group VIII metals in one or more exchanges or conducting one or more exchanges with a first Group VIII metal and subsequent exchanges with a different Group VIII metal. Thus created upon eventual reduction are unique compositions in which colloidal particles of two Group VIII metal having different chemical and electronic properties are entrapped in a single matrix.

One preferred embodiment of these layered metal phosphonate compounds, where Z is a viologen, was found to be very efficient at collecting solar radiation and converting that into stored chemical energy. The active wavelengths for this process are in the ultraviolet portion of the spectrum. The energy storage reaction is evidenced by a deep blue color developing in the solid, which persists for long periods of time in the air. This blue color is due to a reduced viologen compound. Reduced viologen reacts rapidly with oxygen when prepared in solution, but is not reactive in the solid because it is trapped inside the dense solid. Oxygen and other external agents are unable to gain access to the reactive interior layers of the solid.

In order to make it possible to utilize the stored chemical energy in these compounds, a second embodiment comprises a more open structure. The advantage of the open structures is that they will allow external reagents to have ready access to the photogenerated chemical energy. These solids are composed of a mixture of the pillars of the first embodiment further comprising other smaller ligands interspersed among the pillars. These smaller components leave open space in this new solid (see FIG. 4). A wide range of different smaller components having different properties and sizes can be used to prepare these solids, leading to a very diverse family of solids. The general formula for the materials of this second embodiment is:

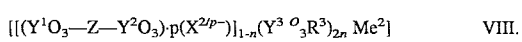

[[(Y$^1$O$_3$—Z—Y$^2$O$_3$)·p(X$^{2/p-}$)]$_{1-n}$(Y$^3$O$_3$R$^3$)$_{2n}$ Me$^2$]   VIII.

wherein each of $Y^1$, $Y^2$, and $Y^3$, independently of the other, is phosphorus or arsenic;

Z is as defined above;

$Me^2$ is a trivalent or tetravalent metal of Group III, IVA, or IVB having an atomic number of at least 21 or a lanthanide;

X is anion;

n has a value of from 0.1 to 0.8;

p is 1 or 2; and $R^3$ is a nonreducible capping group.

In contrast to the materials of the first embodiment which are preferably produced as films on a substrate, the materials of the second embodiment are preferably produced as crystalline or amorphous solids. Analogously to the films of the first embodiment, however, zero valence Group VIII metals can be incorporated in these matrices.

As is apparent from Formula VIII, two distinct ligands complex the metal $Me^2$. The first of these is analogous to that utilized in Formula I, namely $Y^1O_3$—$Z$—$Y^2O_3$, and each such ligand is capable of complexing with two metal atoms. The second ligand, $Y^3O_3R^3$, is capable of complexing with only one metal atom. Thus the overall structure may be viewed as a series of parallel layers of the metals $Me^1$ and $Me^2$ with the $Y^1O_3$—$Z$—$Y^2O_3$ groups serving as pillars. Extending from the metal layers between these pillars are the $Y^3O_3R^3$ groups, forming as it were a series of "stalactites" and "stalagmites" between the pillars. The resultant structure thus has a series of interstices about each —Z— group. The dimensions of these interstices and the hydrophobicity of their defining surfaces can be controlled through selection of $R^3$. Thus one can select relatively small $R^3$ groups such as methyl, creating larger interstices, or relatively larger $R^3$ groups such as phenyl or benzyl, thereby producing relatively smaller interstices. Similarly, one can impart hydrophobic properties to the defining surfaces of the interstices by employing a hydrocarbon group such as propyl for $R^3$ or alternatively decrease the hydrophobicity by employing an $R^3$ group which is substituted with a hydrophilic group such as carboxy. Examples of suitable $R^3$ groups include, but are not limited to: H, $CH_3$, $CH_2Cl$, $CH_2CH_3$, $CH_2CH_2CH_3$, OH, and $OCH_3$. A schematic drawing of these porous solids is shown in FIG. 4.

Because of these interstices, it is possible to introduce Group VIII metals after formation of the complexes, rather than after each step, and then reduce these to zero valence as described above. Hence a complex of Formula VIII is treated with an aqueous solution of a soluble anionic salt of a Group VIII metal and the resulting composition treated with hydrogen to produce the Group VIII metal in colloidal form. These compositions can be used as catalysts as previously described. A schematic drawing of these porous solids is shown in FIG. 5.

Moreover, these interstices permit the passage of various molecules into the complexes. For example, oxygen can enter into the matrices and then oxidize the —Z-groups. Since the reduced form of the —Z-group are colored while the oxidized form is white or yellow, this phenomenon can be used to detect oxygen at extremely low levels. In addition, the ability to control the dimensions of the interstices permits the use of these materials in effecting selective reactions. For example, it is possible to selectively reduce acetophenone in a mixture of acetophenone and 3,5-di-tert. butylacetophenone if the dimensions of the interstices are selected to permit passage of the former molecule but not the latter, more bulky, molecule. The complexes are readily prepared by treating a mixture of $R^3Y^3O_3H_2$ and $H_2Y^1O_3$—Z—$Y^2O_3H_2$ in the desired molar ratio with a source of metal ions. The reaction can be conducted either by refluxing or hydrothermally and the products are readily isolated and purified.

These porous solids show no photochemical activity in the air due to the ready diffusion of oxygen into the interior of the solid. If the porous solids are irradiated with ultraviolet light under anaerobic conditions the same active species, i.e., reduced electron acceptor, observed for the dense solid is formed. Interestingly, the photochemical efficiency of these open solids is much greater than the dense materials. If the porous solids which were irradiated under anaerobic conditions are treated with air, they are rapidly bleached. Oxygen can freely diffuse into the solids and react with the photo-generated reduced electron acceptor. The product of the reaction between the reduced electron acceptor and oxygen is hydrogen peroxide. One could thus use these materials as catalysts for photochemical production of hydrogen peroxide.

It would be desirable to extract the photochemically stored energy by generating mobile high energy chemical species that could diffuse out of the solid. The goal is to incorporate colloidal metal particles into the preferred viologen containing solids. These metals are well known to act as catalysts for the reaction of reduced viologen with water to produce hydrogen gas. Experiments successfully showed that the materials of the second embodiment could be used to convert solar energy into chemical energy in the form of hydrogen gas. The process involved: 1) photo-generation of reduced viologen, 2) electron transfer from reduced viologen to the colloidal metal particle, 3) protonation of the metal particle and 4) elimination of hydrogen gas. Being a true catalyst these materials will accelerate both forward and reverse reactions equally, thus if of "metallized" material is treated with hydrogen some amount of reduced viologen is generated. On this basis these materials can be used as reducing agents. Photochemical energy is not needed to produce reduced viologen: hydrogen can be used to achieve the same result. The process for this chemical generation of reduced viologen is thus: 1) addition of hydrogen to the metal particle, 2) electron transfer from the metal particle to the viologen molecule forming reduced viologen, and 3) deprotonation of the metal colloid. Experiments have shown that the viologen molecules of these materials can be quantitatively reduced with hydrogen gas at atmospheric pressure.

One preferred class of compositions of the second embodiment consists of colloidal particles of Pt and Pd in a porous viologen metal phosphonate matrix (see FIG. 5). These materials are very different from other Pt+Pd catalysts; the viologen groups make a significant difference in the chemistry involved. The oxygen reduction is carried out predominantly by reduced viologen, and not (as is the case in the materials of the DuPont patent) at the colloid surface, perhaps because the rate of reduction of oxygen by reduced viologen is much greater than by the colloidal metal particles. By the nature of the way that the solids are prepared, chloride or bromide "promoters" are unavoidably incorporated. A wide range of different materials were tested. A highly active compound contains a mixture of bisphosphonic acid and phosphate (i.e. $Me(O_3P—OH)_1(O_3P—Z—PO_3)_{0.5-n}$ $H_2O^-Pt/Pd$). Compounds with the phosphate co-ligand where $R^3$ is OH were found to be between 10 and 100 times more active than compounds where $R^3$ was H, $CH_3$, $CH_2Cl$, $CH_2CH_3$, or $CH_2CH_2CH_3$. A wide range of different ratios of Pd:Pt were also tested. The catalysts have been examined to determine their uniformity and composition.

Samples were dissolved in HF and the resulting solutions analyzed by ICP to get the total metal compositions (% by weight of Zr, Pt and Pd, see Table 4). Single particles were analyzed by electron microprobe and found them to have a uniform Zr:Pt:Pd ratio throughout the particles.

A wide range of different electron accepting groups can be associated into this structure that would be amenable to reduction by hydrogen (via colloidal metal particles) and subsequent use as a catalyst for formation of hydrogen peroxide and other reduced species.

The following are results of side-by-side comparisons of the novel catalysts of this invention with other Pt+Pd catalysts which were conducted under identical conditions. (See Table 1.) The amount of noble metal (Pt+Pd) in both the materials of this invention and the other materials were analyzed, and then those analyses were used to scale the amount of catalyst in the experiments to have the same amount of noble metal in each case. The comparisons were performed with mixtures of hydrogen and oxygen at atmospheric pressure. At increased pressures the concentration of hydrogen peroxide at steady state (rates of equations 1 and 2 above are identical so that the concentration of $H_2O_2$ is constant over time) will increase.

TABLE 1

|  | Compound of Ex. 24 (below)† | Other Catalyst‡ |
|---|---|---|
| wt % Pt [i.e., Pt/(Pt + Pd)] | 0.1 | 0.05–0.16 |
| [$H_2O_2$] at steady state (M) (at atmospheric pressure) | 0.14* | 0.07 |
| Initial turnover # ($hr^{-1}$) | 30 |  |

*Actually 0.22 M: In this procedure the solution is brought back up to 10 mL before an aliquot is taken, to compensate for evaporation. The steady state concentration of peroxide (rate of raction 1 = rate of reaction 2) should be constant, regardless of the volume of the sample. Thus when the sample is diluted the amount of peroxide measured is lower. If the conditions of the reaction are the same, giving 0.14 M peroxide, but the reacton mixture is not brought to 10 mL before removing the aliquot the measured concentration is 0.22 M. Thus the steady concentration of peroxide was underestimated by roughly 50%.
†Zr($O_3$POH) ($O_3PCH_2CH_2$bipyridinium$CH_2CH_2PO_3$)Cl⁻Pt⁻Pd-093
‡The best catalyst disclosed in the DuPont patent (U.S. Pat. No. 4,832,938)

A number of different materials according to the present invention, both porous bulk solids and thin films grown on high surface area supports, were prepared and studied. The bulk solids are prepared by:

A) first preparing the layered porous solid:

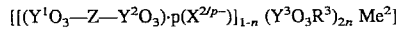  IX.

wherein each of $Y^1$, $Y^2$, and $Y^3$, independently of the other, is phosphorus or arsenic;

Z is as defined above;

$Me^2$ is a trivalent or tetravalent metal of Group III, IVA, or IVB having an atomic number of at least 21 or a lanthanide;

X is anion;

n has a value of from 0.1 to 0.8;

p is 1 or 2; and $R^3$ is a nonreducible capping group.

B) then the halide ions are ion exchanged for polyhalometal anions (such as $PtCl_4^{2-}$); and, C) then the polyhalometal ions are reduced with hydrogen to give a porous solid with impregnated metal particles.

In carrying out the ion exchange reaction it was found that elevated temperatures are needed. At room temperature $PtCl_4^{2-}$ is taken up preferentially over $PdCl_4^{2-}$, leading to a solid that is richer in Pt than the solution it was prepared from. If the ion exchange is carried out at elevated temperatures the exchange is uniform and the composition in the solid matches that of the solution exactly.

The following examples will serve to further typify the nature of the invention but should not be construed as a limitation on the scope thereof which is defined solely by the appended claims.

EXAMPLE 1

Diethyl 2-bromoethylphosphonate (25 g) and 4,4' bipyridine (7.35 g) in 125 mLs of water are refluxed for three days. An equal volume of concentrated hydrochloric acid is added and reflux continued for several hours. The solution is concentrated to 120 mLs by atmospheric distillation and 550 mL of isopropanol are added dropwise with stirring while chilling the mixture in an ice bath. The solid which forms is collected by vacuum filtration and washed with cold isopropanol to yield 1,1'-bisphosphonoethyl-4,4'-bipyridinium dichloride. ($^1$H NMR ($D_2O$) 9.1(d), 8.5(d), 4.2(m), 2.0(m) ppm; $^{13}$C NMR($D_2O$) 151, 147, 128, 58, 30 ppm; $^{31}$P NMR($D_2O$) 17.8 (s) ppm; IR (KBr) 3112, 3014, 1640, 1555, 1506, 1443, 1358, 1281, 1175, 1112, 1020, 936, 816, 485 $cm^{-1}$.)

In a similar fashion, utilizing 2,2-bipyridinium, 3,3-bipyridinium, 2,2-bipyrazinium, 4,4-biquinolinium, 4,4-biisoquninolinium, 4-[2-(4-pyridinium)vinyl]pyridinium, and 4-[4-(4-pyridinium)phenyl]pyridinium, there are respectively obtained 1,1'-bisphosphonoethyl-2,2-bipyridinium dichloride, 1,1'-bisphosphonoethyl-3,3-bipyridinium dichloride, 1,1'-bis-phosphonoethyl-2,2-bipyrazinium dichloride, 1,1'-bisphosphonoethyl-4,4-biquinolinium dichloride, 1,1'-bisphosphonoethyl-4,4-biisoquninolinium dichloride, 1-phosphonoethyl-4-[2-(1-phosphonoethyl-4-pyridinium)vinyl]pyridinium dichloride, and 1-phosphonoethyl-4-[4-(1-phosphonoethyl-4-pyridinium)phenyl]pyridinium dichloride.

Other cationic species, such as the corresponding dibromides or disulfates are obtained by substituting the corresponding acids, such as concentrated hydrobromic acid or sulfuric acid, for hydrochloric acid in the procedure of this example.

EXAMPLE 2

Planar substrates of fused silica (9×25 mm) are cleaned in a 1:3 solution of 30% hydrogen peroxide and conc. sulfuric acid, dried at 200° C. for one hour, and then treated with a refluxing solution of 2% (v/v) 3-aminopropyltriethoxysilane in 50 mL of octane for 20 minutes.

The substrates are rinsed with octane and acetonitrile and treated for 12 hours at room temperature with a solution of 10 mM each of phosphoryl chloride and 2,6-lutidine in acetonitrile. After rinsing in water, the substrates are treated with a 65 mM solution of zirconyl chloride for three hours at room temperature.

The foregoing procedure can be used to prepare multilayer films on other substrates such as silicon wafers and vapor deposited gold films.

The substrate next is subjected sequentially to the following two steps.

A). After removal of the solution of zirconyl chloride, the samples are thoroughly rinsed with deionized water and treated with 6 mM of 1,1'-bisphosphonoethyl-4,4'-bipyridinium dichloride at 80° C. for 4 hours and then thoroughly rinsed with deionized water. (Absorption is measured at 284 nm after treatment, the measured extinction coefficient for 4,4'-bipyridinium bisphosphonate being 24,000M$^{-1}$ cm$^{-1}$ at 265 nm.)

B). The samples next are treated with a 65 mM zirconyl chloride solution at room temperature for one hour and again thoroughly rinsed with deionized water.

Upon completion of one cycle of steps A and B, a plurality of a metal complex of Formula I in which k is 1 is obtained on the planar silica supporting substrate. Each repetition of steps A and B increases the value of k by one. The number of layers, and thus the number of cycles, correlates to absorbance at 284 nm, as can be seen from the following:

| No. of Layers | Absorbance |
|---|---|
| 0 | 0.057 |
| 1 | 0.083 |
| 2 | 0.091 |
| 3 | 0.109 |
| 4 | 0.130 |
| 5 | 0.152 |
| 6 | 0.177 |
| 7 | 0.201 |
| 8 | 0.217 |
| 9 | 0.242 |
| 10 | 0.263 |
| 11 | 0.281 |
| 12 | 0.299 |
| 13 | 0.327 |
| 14 | 0.341 |
| 15 | 0.357 |
| 16 | 0.367 |
| 17 | 0.373 |
| 18 | 0.383 |
| 19 | 0.407 |
| 20 | 0.423 |
| 21 | 0.452 |
| 22 | 0.458 |

EXAMPLE 3

By substituting 1,1'-bisphosphonoethyl-4,4'-bipyridinium dibromide in the procedure of Example 2, a series of multi-laminar compositions are obtained having the following absorbances:

| No. of Layers | Absorbance |
|---|---|
| 1 | 0.083 |
| 2 | 0.098 |
| 3 | 0.113 |
| 4 | 0.157 |
| 5 | 0.182 |
| 6 | 0.239 |
| 7 | 0.286 |
| 8 | 0.350 |
| 9 | 0.353 |
| 10 | 0.391 |
| 11 | 0.465 |
| 12 | 0.557 |

EXAMPLE 4

High quality films also are obtained by employing other metals in place of zirconium in step B, e.g., hafnium, titanium, tin, gallium, etc, as shown in the following procedure.

Planar fused silica substrates (9×25 mm) are cleaned as described in Example 2 and a layer of 3-aminopropyltriethoxysilane is deposited thereon from the gas phase using the method of Haller, *J. Am. Chem. Soc.*, 100, 8050 (1978). The substrates are phosphorylated as described in Example 2, rinsed, and treated with 10 mL of a 65 mM aqueous solution of hafnyl chloride for three hours at room temperature.

Alternating treatments with (A) an aqueous solution containing 6 mM 1,1'-bisphosphonoethyl-4,4'-bipyridinium dibromide and 20 mM sodium chloride at 80° C. for 4 hours and (B) a 65 mM aqueous solution hafnyl chloride at room temperature for 1 hour, with thorough rinsing with deionized water after each, then produce a series of multi-laminar compositions which can be characterized spectrophotometrically at 284 nm.

| No. of Layers | Absorbance |
|---|---|
| 1 | 0.052 |
| 2 | 0.086 |
| 4 | 0.175 |
| 6 | 0.250 |
| 8 | 0.304 |
| 10 | 0.384 |
| 12 | 0.518 |

EXAMPLE 5

The procedure of Example 2 is modified after one or more executions of step A but before execution of the corresponding step B by immersing the samples in a 6 mM aqueous solution of dipotassium platinum tetrachloride for 0.5 hour thereby exchanging one platinum tetrachloride anion for two chloride anions. Step B then is performed as described in Example 2.

After completing the final cycle of steps A and B, the composite is suspended in water and hydrogen gas is bubbled through the mixture for two hours. The platinum is reduced to a zero valence colloidal state entrapped in the overall matrix.

EXAMPLE 6

Silica particles (1 g) are heated in a drying oven for one hour and then stirred with 150 mL of an aqueous solution (60 mM) of zirconyl chloride with the silica (1 g) at 60° C. for two days. The solid is isolated by filtration or centrifugation, washed three times with 150 mL of deionized water, and treated with 150 mL of a 20 mM solution of the 1,1'-bisphosphonoethyl-4,4'-bipyridinium for six hours at 65° C. with agitation. The solid is separated from the aqueous solution and washed three times with deionized water.

The solid then is treated with 150 mL of a 20 mM solution of potassium platinum hexachloride for three hours at room temperature, thereby exchanging one platinum hexachloride anion for two chloride anions.

One hundred and fifty milliliters of a 60 mM solution of zirconyl chloride are added to the solid and the slurry agitated for three hours at room temperature and washed three times with deionized water.

The foregoing steps are repeated four times to produce a pentalaminar composition containing platinum cations. Treatment of an aqueous slurry of the platinized materials with hydrogen then converts the platinum ions into colloidal zero valence platinum metal.

EXAMPLE 7

A substrate of gold deposited on a chromium metal film in turn deposited on glass is treated first with 3-aminopropyltriethoxysilane and then phosphoryl chloride as previously described and then subjected to the procedure of Example 2 three times to prepare a composition of Formula I in which k is 3.

This composition shows a reversible reduction wave at −0.74 V versus a saturated calomel electrode. In water, it shows an irreversible reduction below −1.4 V versus the same standard electrode.

EXAMPLE 8

Twenty-five milligrams of a composition prepared as set forth in Example 6 in 5 mL of 0.1M disodium ethylenediaminetetraacetic acid as a sacrificial reductant in 1 cm$^2$ cell is irradiated with a 200 Watt Hg/Xe lamp. Levels of hydrogen are measured by gas chromatography. The rate of hydrogen production over 18 hours of photolysis is 0.07 mL/hr. Passing the light through a 330 nm cutoff filter (G>330 nm) decreases the rate of hydrogen production by more than an order of magnitude. If the filter is removed the sample photogenerates hydrogen as before. The quantum yield for hydrogen formation (2 xmoles of H$_2$/moles of photons incident with G<330 nm) in this system is 0.008.

EXAMPLE 9

Zirconyl chloride octahydrate (1.444 g, 4.8 mmol.) is dissolved in 50 mLs water and 50% hydrofluoric acid (0.756 g, 19 mmol) are added. To this is added a solution of 1 g of 1,1'-bisphosphonoethyl-4,4'-bipyridinium dichloride (2.2 mmol) and 0.516 g of 85% phosphoric acid (4.5 mmol.) in 50 mLs of water. The reaction is refluxed for seven days and the white crystalline product is filtered and washed with water, methanol, and acetone and air-dried to yield the mixed complex:

X-Ray diffraction analysis shows d=14Å. Infra red analysis is as follows: (IR (cm−1), 3126, 3056, 1633, 1562, 1499, 1450, 1217, 1055, 816, 738, 647, 612, 520, 471). $^{31}$P NMR (ppm) are: 3.0, −18.6, −24.5.

EXAMPLE 10

Zirconyl chloride octahydrate (0.21 g, 0.7 mmol.) is dissolved in 10 mLs water and 50% hydrofluoric acid (0.11 g, 2.8 mmol) are added. To this is added a solution of 0.15 g of 1,1'-bisphosphonoethyl-4,4'-bipyridinium dichloride (0.35 mmol) and 0.0686 g of 85% phosphoric acid (0.6 mmol.) in 10 mLs of water. The solution is placed in a 45 mL teflon bomb and the total volume adjusted to 27 mLs. The bomb is sealed and heated at 150° C. for six days to yield the mixed complex:

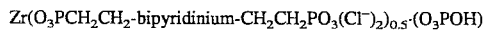

X-Ray diffraction analysis shows d=14Å. Infra red and $^{31}$P NMR (ppm) are identical to those given in Example 9.

EXAMPLE 11

Zirconyl chloride octahydrate (0.36 g, 1.12 mmol.) is dissolved in 10 mLs water and 50% hydrofluoric acid (0.179 g, 4.5 mmol) are added. To this is added a solution of 0.25 g of 1,1'-bisphosphonoethyl-4,4'-bipyridinium dichloride (0.56 mmol) and 0.129 g of 85% phosphoric acid (0.11 mmol.) in 50 mLs of 3N hydrochloric acid. The reaction is refluxed for seven days and the white crystalline product is filtered and washed with water, methanol, and acetone and air-dried to yield the mixed complex:

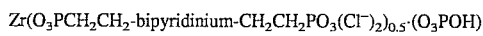

X-Ray diffraction analysis shows d=18.5Å. Infra red and $^{31}$P NMR (ppm) are identical to those given in Example 9.

EXAMPLE 12

Zirconyl chloride (octahydrate) (0.361 g, 1.12 mmol.) is dissolved in 10 mLs water and 0.189 g of 50% hydrofluoric acid (4.8 mmol.) is added. 1,1'-Bisphosphonoethyl-bipyridinium dichloride (0.25 g, 0.56 mmol.) and phosphorous acid (0.092 g, 1.12 mmol.) are dissolved in 10 mLs of water and this solution is added to the aqueous zirconium solution. The reaction is refluxed for seven days and the white crystalline product is filtered, washed with water, methanol, and acetone and air-dried to yield the mixed complex:

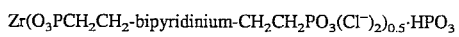

X-Ray diffraction analysis shows d=18.4 Å. Infra red analysis is as follows: 3126, 3056, 2436, 2358, 2330, 1633, 1555, 1499, 1443, 1386, 1210, 1161, 1048, 830, 731, 548. $^{31}$P NMR (ppm) are: 5.5, −9.5.

EXAMPLE 13

By following the procedure of Example 10 but utilizing 0.167 (0.38 mmol.) of 1,1'-bisphosphonoethyl-bipyridinium dichloride and 0.123 g (1.5 mmol.) of phosphorous acid, there is obtained the mixed complex:

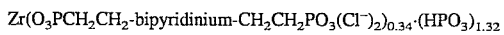

The material is amorphous. Infra red and $^{31}$P NMR (ppm) are identical to those given in Example 12.

EXAMPLE 14

By following the procedure of Example 12 but utilizing 0.125 (0.28 mmol.) of 1,1'-bisphosphonoethyl-bipyridinium dichloride and 0.138 g (1.68 mmol.) of phosphorous acid, there is obtained the mixed complex:

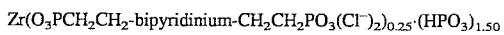

The material is amorphous. Infra red and $^{31}$P NMR (ppm) are identical to those given in Example 12.

EXAMPLE 15

Zirconyl chloride (octahydrate) (0.151 g, 0.47 mmol.) is dissolved in 10 mLs water and 50% hydrofluoric acid (0.079 g, 1.9 mmol.) is added. 1,1'-bisphosphonoethyl-bipyridinium dichloride (0.105 g, 0.24 mmol.) and methyl phosphonic acid (0.045 g, 0.47 mmol.) are dissolved in 10 mLs of water and this solution is added to the aqueous zirconium solution. The reaction is refluxed for seven days and the white crystalline product is filtered, washed with water, methanol, and acetone and air-dried to yield the mixed complex:

The material is amorphous. Infra red analysis is as follows: (IR (cm−1), 3450, 3133, 3056, 2922, 1633, 1555, 1499, 1450, 1309, 1168, 1027, 823, 781, 527).

EXAMPLE 16

In a similar fashion to that described in Example 10, 0.93 mmol. of zirconyl chloride, 0.34 mmol. of 1,1'-bisphosphonoethyl-bipyridinium dichloride, and 0.90 mmoles of 3-aminoethylphosphonic acid are heated in a bomb at 150° C. Upon isolation as therein described the amorphous mixed complex exhibits the following IR spectra: (IR (cm–1), 3500, 3126, 3055, 1646, 1548, 1499, 1443, 1379, 1154, 1041, 865, 823, 760, 731, 541, 499.

EXAMPLE 17

In a similar fashion to that described in either Example 9 or Example 10, zirconyl chloride, 1,1'-bisphosphonoethyl-bipyridinium dichloride, and a phosphorus-containing co-ligand as shown in the following table are allowed to react.

TABLE 2

| Co-ligand Reagent | mmols. | BPBP* (mmols.) | ZrOCl$_2$ (mmols.) | Conditions |
|---|---|---|---|---|
| CH$_3$PO(OH)$_2$ | 0.47 | 0.23 | 0.47 | Ex. 8: 150° C. |
| CH$_3$CH$_2$PO(OH)$_2$ | 1.12 | 0.56 | 1.12 | Ex. 7 |
| CH$_3$CH$_2$CH$_2$PO(OH)$_2$ | 0.94 | 0.47 | 0.94 | Ex. 8: 200° C. |
| CH$_3$CH$_2$CH$_2$PO(OH)$_2$ | 0.83 | 0.41 | 0.80 | Ex. 8: 140° C. |
| HOCOCH$_2$CH$_2$PO(OH)$_2$ | 0.30 | 0.19 | 0.15 | Ex. 8: 110° C. |
| PhenylPO(OH)$_2$ | 1.12 | 0.56 | 1.12 | Ex. 7 |
| ClCH$_2$PO(OCH$_2$CH$_3$)$_2$ | 1.12 | 0.56 | 1.12 | Ex. 7 |
| BenzylPO(OCH$_2$CH$_3$)$_2$ | 0.70 | 0.33 | 0.65 | Ex. 7 |

*BPBP = 1,1'-bisphosphonoethyl-bipyridinium dichloride

Thereby produced are mixed complexes of the formula:

Zr(O$_3$PCH$_2$CH$_2$-bipyridinium-CH$_2$CH$_2$PO$_3$(Cl$^-$)$_2$)$_{0.5}$·R$^3$PO$_3$ Data on these products are as follows:

TABLE 3

| R$^3$ | X-ray | IR Data |
|---|---|---|
| —CH$_3$ | * | See Ex. 13 |
| —CH$_2$CH$_3$ | d = 10.9Å* | Spectra I |
| —CH$_2$CH$_2$CH$_3$ | d = 11.8Å* | Spectra II |
| —CH$_2$CH$_2$CH$_3$ | d = 13.6Å* | Spectra II |
| —CH$_2$CH$_2$COOH | d = 15.4Å | Spectra III |
| -phenyl | d = 19.7Å* | Spectra IV |
| —CH$_2$Cl | d = 11Å* | Spectra V |
| -benzyl | d = 14.5Å | Spectra VI |

* = Peaks present which are attributable to pure metal bisphosphonate.
Spectra I: (IR(cm-1), 3507, 3126, 3056, 2978, 2943, 2887, 1640, 1563, 1506, 1450, 1393, 1281, 1168, 1048, 872, 830, 738, 541.
Spectra II: (IR (cm-1), 3500, 3126, 3049, 2950, 2866, 1633, 1555, 1499, 1450, 1393, 1246, 1041, 872, 823, 795, 731, 541.
Spectra III: (IR (cm-1), 3500, 2915, 1717, 1633, 1415, 1260, 1027, 816, 752, 534.
Spectra IV: (IR (cm-1), 3500, 3126, 3049, 1633, 1555, 1499, 1443, 1386, 1161, 1055, 865, 823, 749, 731, 710, 541.
Spectra V: (IR (cm-1), 3500, 3119, 3049, 1633, 1555, 1499, 1443, 1386, 1161, 1055, 865, 823, 759, 731, 710, 541.
Spectra VI: (IR (cm-1), 3500, 3126, 3056, 1633, 1598, 1492, 1450, 1386, 1253, 1161, 1034, 830, 781, 738, 696, 626, 541, 499.

EXAMPLE 18

Zr(O$_3$PCH$_2$CH$_2$-bipyridinium-CH$_2$CH$_2$PO$_3$(Cl$^-$)$_2$)$_{0.5}$(O$_3$POH), the complex prepared as in Example 7 (0.05 g) is stirred with 10 mLs of a 10 mM aqueous solution of dipotassium platinum tetrachloride at room temperature for two days. Over the course of the reaction, the solid changes from white to yellow. The solid then is isolated by filtration, washed extensively with deionized water, and air dried. The solid is suspended in deionized water and hydrogen gas bubbled through the mixture for ten hours. The solid changes from yellow to dark purple. The solid is isolated by filtration, washed with deionized water, and air dried to give a brown solid.

Zr(O$_3$POH)(O$_3$PCH$_2$CH$_2$bipyridiniumCH$_2$CH$_2$PO$_3$)Cl for the following examples was prepared as in Examples 9, 10, and 11 above. Various ratios of platinum and palladium were then incorporated as follows:

EXAMPLE 19

Zr(O$_3$POH)(O$_3$PCH$_2$CH$_2$bipyridiniumCH$_2$CH$_2$PO$_3$)Cl$^-$ Pt: 200 mg of Zr(O$_3$POH)(O$_3$PCH$_2$CH$_2$bipyridiniumCH$_2$CH$_2$PO$_3$)Cl was treated with 2 ml of 5.1×10$^{-3}$M solution of K$_2$PtCl$_4$ at 60° C. for 1 hr. The solid was filtered, washed, and hydrogenated as mentioned in the previous example. 0.0162 g of the solid was used to prepare a 25 ml solution for the analysis to give Zr=117.9 ppm; Pt=20.01 ppm

EXAMPLE 20

Zr(O$_3$POH)(O$_3$PCH$_2$CH$_2$bipyridiniumCH$_2$CH$_2$PO$_3$)Cl$^-$ Pd: 100 mg of Zr(O$_3$POH)(O$_3$PCH$_2$CH$_2$bipyridiniumCH$_2$CH$_2$PO$_3$)Cl and 1 ml of 6.3×10$^{-2}$M PdCl$_2$ was treated at 60° C. for 4 hrs. The orange solid was filtered, washed, and hydrogenated as before. 0.0131 g of the solid was dissolved in 25 ml as mentioned above for analysis to give Zr=92.96 ppm; Pd=8.54ppm.

EXAMPLE 21

Zr(O$_3$POH)(O$_3$PCH$_2$CH$_2$bipyridiniumCH$_2$CH$_2$PO$_3$)Cl$^-$ Pt$^-$Pd-58: 170 mg of Zr(O$_3$POH)(O$_3$PCH$_2$CH$_2$bipyridiniumCH$_2$CH$_2$PO$_3$)Cl was mixed with 4.6 ml of PdCl$_2$(7.3×10$^{-3}$M) and 2.8 ml of K$_2$PtCl$_4$(6.1×10$^{-3}$M). This mixture was heated to 60° C. with constant stirring for 1 hr. The yellow powder was filtered and washed three to four times with water. The yellow solid was suspended in water and hydrogen gas was bubbled for ½ hr at 60° C. The gray/black solid was filtered and washed first with water and then with ethanol. This solid was then air dried. 0.0072 g of the above solid was dissolved in conc. HCl, a few drops of conc. HNO3, and a few drops of 59% HF. The solution was diluted to 100 ml. and analyzed for Zr, Pt, and Pd by ICP. The analysis (ppm) of the solution are Zr=14.05; Pt=1.01; Pd=0.73

EXAMPLE 22

Zr(O$_3$POH)(O$_3$PCH$_2$CH$_2$bipyridiniumCH$_2$CH$_2$PO$_3$)Cl$^-$ Pt$^-$Pd-32: 260 mg of Zr(O$_3$POH)(O$_3$PCH$_2$CH$_2$bipyridiniumCH$_2$CH$_2$PO$_3$)Cl and 3 ml solution of 0.11M K$_2$PdCl4 and 6.4×10$^{-3}$M K$_2$PtCl$_4$ was heated to 60° C. for 30 minutes with constant stirring. The yellow solid so obtained was filtered and washed several times with water. This solid was resuspended in water and treated with $H_2$ gas as mentioned in the first synthesis. 0.0136 g of the dried solid was dissolved and analyzed as before, values in ppm: Zr=24.72; Pt=0.69; Pd=1.5.

EXAMPLE 23

$Zr(O_3POH)(O_3PCH_2CH_2bipyridiniumCH_2CH_2PO_3)Cl^-$ Pt⁻Pd-00: 200 mg of $Zr(O_3POH)(O_3PCH_2CH_2bipyridiniumCH_2CH_2PO_3)Cl$ was treated with 1 ml of 0.11M $K_2PdCl_4$ and 0.18 ml of $1.6\times10^{-3}$M $K_2PtCl_4$ and hydrogenated as mentioned in the previous example.) 0.0117 g of the final black solid was dissolved in conc. HCl, a few drops of conc. HNO3, and a few drops of 50% HF. This solution was diluted to 25 ml. The analysis of the solution is as follows: Zr(ppm)=48.92; Pt=not detected; Pd(ppm)=6.75.

EXAMPLE 24

$Zr(O_3POH)(O_3PCH_2CH_2bipyridiniumCH_2CH_2PO_3)Cl^-$ Pt⁻P d-30: 200 mg of $Zr(O_3POH)(O_3PCH_2CH_2bipyridiniumCH_2CH_2PO_3)Cl$, 1 ml of $4.8\times10^{-2}$M $K_2PdCl_4$, and 0.275 ml of $4.7\times10^{-2}$M $K_2PtCl_4$ was stirred at 60° C. for 20 min. The yellow solid so obtained was filtered, washed with water, and hydrogenated as before. 0.0125 g of the solid was dissolved as before and diluted to 25 ml for analysis to give Zr=49.91 ppm, Pt=2.15 ppm, Pd=4.92 ppm.

EXAMPLE 25

$Zr(O_3POH)(O_3PCH_2CH_2bipyridiniumCH_2CH_2PO_3)Cl^-$ Pt⁻PD-11: 500 mg of $Zr(O_3POH)(O_3PCH_2CH_2bipyridiniumCH_2CH_2PO_3)Cl$ was refluxed for 6 hrs. with 15 ml of $7.4\times10^{-3}$M $PdCl_2$ and 0.99 ml of $5.1\times10^{-3}$M $K_2PtCl_4$. The solid was filtered, washed and as before. The hydrogenation of the solid was carried as before except for 1 hr. 0.0172 g of this solid was dissolved as before and diluted to 25 ml for analysis to give Zr=70.29 ppm; Pt=1.18 ppm; Pd=9.10 ppm.

EXAMPLE 26

$Zr(O_3POH)(O_3PCH_2CH_2bipyridiniumCH_2CH_2PO_3)Cl^-$ Pt⁻Pd-093: 500 mg of $Zr(O_3POH)(O_3PCH_2CH_2bipyridiniumCH_2CH_2PO_3)Cl$, 15 ml of $7.4\times10^{-3}$M $PdCl_2$ and 0.99 ml of $5.1\times10^{-3}$M $K_2PtCl_4$ was refluxed for 65 hrs. Filtered, washed, and hydrogenated as mentioned in the previous example. 0. g of the solid was dissolved as before and diluted to 25 ml for analysis to give Zr=127.98 ppm; Pt=0.78 ppm; Pd=7.72 ppm.

Materials were grown on high surface area supports in a multistep process, as described below. Ion exchange can be carried out either as the film is growing or after it is prepared.

EXAMPLE 27

Synthesis of $SiO_2^-$ $Zr(O_3POH)(O_3PCH_2CH_2bipyridiniumCH_2CH_2PO_3)Cl^-$:

One gram of silica gel (Selecto, Inc. Cat#162544, lot #216073) was heated at 200° C. for 1 hr. This was treated with 150 ml of 65 mM $ZrOCl_2$ at 60° C. for two days. This was followed by a treatment with 150 ml solution, which consists of 20 mM $(O_3PCH_2CH_2bipyridiniumCH_2CH_2PO_3)Cl$, 20 mM phosphoric acid, and 60 mM NaCl at 60° C. for 18 hours. These treatments were repeated four times. At the end the pale yellow solid was washed with water and dried.

EXAMPLE 28

$SiO_2^-$ $Zr(O_3POH)(O_3PCH_2CH_2bipyridiniumCH_2CH_2PO_3)Cl^-Pt^-$ Pd-21: 270 mg of $SiO_2^-$ $Zr(O_3POH)(O_3PCH_2CH_2bipyridiniumCH_2CH_2PO_3)Cl$ was treated with 3 ml solution, which was 0.12M in $K_2PdCl_4$ and $6.4\times10^{-3}$M in $K_2PtCl_4$ at 60° C. for one hour. Filtered and washed. The solid was hydrogenated as mentioned above. 0.0494 g of this solid was dissolved and in HCl, $HNO_3$, and 50 HF and diluted to 25 ml. Analyses: Zr=166.8 ppm, Pt=2.97 ppm, Pd=10.89 ppm.

EXAMPLE 29

Samples were prepared as described above in the synthesis of each compound. The metal content of these solutions were then determined by ICP, in the departmental analytical facility in the Geological and Earth Sciences Department at Princeton. The individual numbers listed in the tables are the weight percent of that element in the sample. The weight percent of viologen was estimated from the Zr value, assuming there are 2 Zr atoms per viologen molecule in the solid. The viologen unit in this case was taken to be $C_{10}H_8N_2$.

TABLE 4

Elemental analyses of all compounds listed in this disclosure (ICP on dissolved samples).

| COMPOUND | R (obs) | R (theo) | % Pt | % Pd | % Zr |
| --- | --- | --- | --- | --- | --- |
| Du-D, sample 1 | 0.02 | 0.08 | 0.01 | 0.38 | 0 |
| DU-D, sample 2 | 0.08 | 0.093 | 0.02 | 0.23 | 0 |
| DU-F | 0.2 | 0.3 | 0.05 | 0.2 | 0 |
| DU-H | 0.65 | 0.7 | 0.15 | 0.08 | 0 |
| Zr*PV(POH)*Pd | 0 | 0 | 0 | 1.63 | 17.74 |
| Zr*PV(POH)*Pt*Pd-005 | 0 | 0.005 | not detected | 1.44 | 17.24 |

TABLE 4-continued

Elemental analyses of all compounds listed in this disclosure (ICP on dissolved samples).

| COMPOUND | R (obs) | R (theo) | % Pt | % Pd | % Zr |
|---|---|---|---|---|---|
| Zr*PV(POH)*Pt*Pd-093 | 0.092 | 0.093 | 0.11 | 1.07 | 17.78 |
| Zr*PV(POH)*Pt*Pd-11 | 0.16 | 0.093 | 0.32 | 1.65 | 16.37 |
| Zr*PV(POH)*Pt*Pd-14 | 0.14 | 0.09 | 2.42 | 1.48 | 18.29 |
| Zr*PV(POH)*Pt*Pd-30 | 0.29 | 0.14 | 0.43 | 1.17 | 18.71 |
| Zr*PV(POH)*Pt*Pd-32 | 0.32 | 0.093 | 0.51 | 1.1 | 18.18 |
| Zr*PV(POH)*Pt*Pd-58 | 0.58 | 0.49 | 1.4 | 1.01 | 19.51 |
| Zr*PV(POH)*Pt | 1 | 1 | 3.09 | 0 | 18.19 |
| Zr*PV(POH)*Pd + PtCl$_4$ | 0.85 | Unknown | 3.86 | 0.66 | 46.56 |
| Zr*PV*Pt | 1 | 1 | 4.3 | 0 | 12.35 |
| Zr*PV(PH)*Pt | 1 | 1 | 7.96 | 0 | 14.87 |
| Zr*PV(POH)*Pt + PdCl$_4$ | 0.6 | Unknown | 2.35 | 1.57 | 16.55 |
| SiO$_2$*Zr*PV(POH)*Pt*Pd-11 | .11 | 0.093 | 0.1 | 0.78 | 8.06 |
| SiO$_2$*Zr*PV(POH)*Pt*Pd-21 | .21 | 0.093 | 0.15 | 0.55 | 8.7 |
| SiO$_2$*Zr*PV(POH)*Pt*Pd-27 | .27 | 0.093 | 0.35 | 0.9 | 2.67 |

Definitions for Table 4:
DU-D: DuPont's Patent U.S. Pat. No. 4,832,938 Table 1 A prep D.
DU-F: DuPont's Patent U.S. Pat. No. 4,832,938 Table 1 A prep.F.
DU-H: DuPont's Patent U.S. Pat. No. 4,832,938 Table 1 A prep.H.
Zr*PV(POH) = Zr(O$_3$POH) (O$_3$PCH$_2$CH$_2$bipyridiniumCH$_2$CH$_2$PO$_3$)Cl
Zr*PV(PH) = Zr(O$_3$PH) (O$_3$PCH$_2$CH$_2$bipyridiniumCH$_2$CH$_2$PO$_3$)Cl
Zr*PV = Zr(O$_3$PCH$_2$CH$_2$bipyridinium CH$_2$CH$_2$PO$_3$)Cl
R = Pt/(Pt + Pd) (wt./wt.)
R (obs.) = The ratio calculated from the analysis of Pt and Pd by ICP.
R (theo) = The ratio calculated from the initial concentrations of Pt and Pd in the reacting solution.

Hydrogen Peroxide Formation:

As mentioned earlier, the materials of the present invention can be used as catalysts for the production of hydrogen peroxide. The process comprises treating an aqueous suspension of the catalyst with a source of oxygen and a source of hydrogen. Sources for oxygen include pure oxygen, air, ozone or any nitrogen oxide. The suspension can also contain acids or bases to control the pH of the system.

EXAMPLE 30

For the data in the tables listed below a known amount of catalyst was placed in a 50 ml plastic tube. 10 ml of 0.15 mM solution of acetanilide in 0.1M HCl was added to the tube, and it was sealed with a rubber septum. A mixture of oxygen and hydrogen was bubbled through the suspension. In some cases air was used rather than $O_2$ and are identified as such, in those cases the ratios listed are the ratio of hydrogen to oxygen not hydrogen to air. After the prescribed amount of time the loss of solution volume due to evaporation is made up by the addition of 0.15 mM solution of acetanilide in 0.1M HCl. A known amount of reaction mixture was withdrawn and diluted to 5 ml with titanium sulfate solution previously prepared in sulfuric acid. The absorbance of this solution was recorded at 410 nm. This colorimetric assay has been checked by titration of the same solutions with $KMnO_4$ and shown to be very accurate.

The data listed in Table 5 represents $H_2O_2$ production for two preferred materials according to the present invention and some other catalysts. Table 6 show similar test data for other compounds according to the present invention and other compounds. Table 7 shows data collected for a several different ratios of Pt to Pd in the catalyst. Table 8 shows data at a number of pHs.

TABLE 5

Hydrogen peroxide formation, pH = 1 atm. The amount of catalysts used in each experiment was adjusted to give a constant number of moles of Pd + Pt in each experiment.

| Compound | Gas Ratio $H_2:O_2$ | Amount of Catalyst (mg) | Time (hrs.) | $|H_2O_2|$ (mM) | Initial Turnover # |
|---|---|---|---|---|---|
| Zr.PV(POH).Pt.Pd-093 | 1:1 | 22 | 1 | 12 | 10.8 |
| | | | 2.5 | 28 | |
| | | | 5 | 43 | |
| | | | 7 | 44 | |
| | | | 8.5 | 50 | |
| | | | 24 | 99 | |
| | 1:5 | 23 | 1.3 | 33 | 29.4 |
| | | | 2.3 | 51 | |
| | | | 4.6 | 71 | |
| | | | 6.3 | 79 | |
| | | | 8.3 | 80 | |
| | | | 24 | 140 | |
| | 1:10 | 22 | 1 | 10 | 8.8 |
| | | | 2.2 | 21 | |
| | | | 3.5 | 29 | |
| | | | 5.0 | 37 | |
| | | | 7.3 | 48 | |
| | | | 22 | 101 | |
| | 1:20 | 24 | 1 | 11 | 10 |
| | | | 2.4 | 28 | |
| | | | 4.2 | 39 | |
| | | | 5.7 | 53 | |
| | | | 8.2 | 71 | |
| | 1:40 | 23 | 1 | 2.4 | 2.4 |
| | | | 3.5 | 28 | |
| | | | 5.5 | 45 | |
| | | | 7.5 | 54 | |
| | | | 23 | 88 | |
| | | | 26 | 79 | |
| | | | 28 | 76 | |
| SiO$_2$.Zr.PV(POH).Pt.Pd-21 | 1:5 | 44 | 1 | 10 | 10 |
| | | | 2.5 | 22 | |
| | | | 4 | 31 | |
| | | | 6.5 | 33 | |
| | | | 8.3 | 33 | |
| | | | 9 | 33 | |
| DU-D, Sample 2 | 1:5 | 118 | 1 | 16 | |
| | | | 2.9 | 31 | |
| | | | 3.9 | 38 | |
| | | | 5.9 | 49 | |
| | | | 7.9 | 58 | |
| | | | 23 | 77 | |
| DU-H | 1:5 | 128 | 1.1 | 16 | |
| | | | 2.5 | 24 | |
| | | | 4 | 32 | |
| | | | 7.3 | 36 | |
| | | | 23 | 50 | |
| | | | 26 | 50 | |
| | | | 28 | 50 | |
| DU-F | 1:5 | 122 | 1 | 10 | |
| | | | 2.3 | 19 | |
| | | | 4 | 30 | |
| | | | 6 | 44 | |
| | | | 9 | 58 | |
| | | | 24 | 46 | |

DU-D: DuPont's Patent U.S. Pat. No. 4,832,938 Table 1 A prep D.
DU-F: DuPont's Patent U.S. Pat. No. 4,832,938 Table 1 A prep.F.
DU-H: DuPont's Patent U.S. Pat. No. 4,832,938 Table 1 A prep.H.
Zr*PV(POH) = Zr(O$_3$POH) (O$_3$PCH$_2$CH$_2$bipyridiniumCH$_2$CH$_2$PO$_3$)Cl
Zr*PV(PH) = Zr(O$_3$PH) (O$_3$PCH$_2$CH$_2$bipyridiniumCH$_2$CH$_2$PO$_3$)Cl
Zr*PV = Zr(O$_3$PCH$_2$CH$_2$bipyridinium CH$_2$CH$_2$PO$_3$)Cl
Pd-Pt-# refers to Pt/(Pt + Pd) (wt./wt.)

TABLE 6

Comparison of DuPont catalysts and novel catalysts according to the present invention using an $H_2:O_2$ ratio of 2:1 ($O_2$ from air) at pH = 1. The amount of catalyst used in each experiment was adjusted to give a constant number of moles of Pd + Pt in each experiment.

| COMPOUND | Quantity (mg) | $H_2O_2$ (mM) at 18 hours | $H_2O_2$ (mM) at 45 hours | Mole % Pd |
|---|---|---|---|---|
| DU-D | 152 | 4.6 | 1.0 | 0.545 |
| DU-F | 246 | 2.2 | 0.5 | 0.464 |
| DU-H | 262 | 4.6 | 4.5 | 0.200 |
| Zr.PV(POH).Pt.Pd-58 | 25 | 12.5 | 2.6 | 0.238 |
| Zr.PV(POH).Pt.Pd-32 | 38 | 22.5 | 15.1 | 0.394 |
| Zr.PV(POH).Pt.Pd-30 | 42 | 18.3 | 9.0 | 0.386 |
| Zr.PV(POH).Pt.Pd-00 | 43 | 13.7 | 10.1 | 0.584 |
| $SiO_2$.Zr.PV(POH).Pt.Pd-27 | 49 | 3.5 | 2.6 | 0.416 |
| Zr.PV.Pt | 25 | 0.5 | | |
| Zr.PV(PH).Pt | 40 | 0.6 | | |
| Zr.PV(POH).Pt | 30 | 5.5 | | |

DU-D: DuPont's Patent U.S. Pat. No. 4,832,938 Table 1 A prep D.
DU-F: DuPont's Patent U.S. Pat. No. 4,832,938 Table 1 A prep.F.
DU-H: DuPont's Patent U.S. Pat. No. 4,832,938 Table 1 A prep.H.
Zr*PV(POH) = $Zr(O_3POH)$ $(O_3PCH_2CH_2bipyridiniumCH_2CH_2PO_3)Cl$
Zr*PV(PH) = $Zr(O_3PH)$ $(O_3PCH_2CH_2bipyridiniumCH_2CH_2PO_3)Cl$
Zr*PV = $Zr(O_3PCH_2CH_2bipyridinium\ CH_2CH_2PO_3)Cl$
Pd-Pt-# refers to Pt/(Pt + Pd) (wt./wt.)

TABLE 7

$H_2O_2$ production from catalysts with different amounts of Pt (different R values) 2:1 mixture to $H_2:O_2$ (air was used as an oxygen source) 1 atm, pH = 1

| COMPOUND | Quantity (mg) | Time (hrs.) | $H_2O_2$ (mM) |
|---|---|---|---|
| Zr.PV(POH).Pt.Pd-005 | 28 | 1 | 2.2 |
| | | 23 | 2.5 |
| | | 27.5 | 2.5 |
| | | 30 | 2.7 |
| Zr.PV(POH).Pt.Pd-11 | 29 | 1 | 2.8 |
| | | 23 | 4.5 |
| | | 27.5 | 5.8 |
| | | 30 | 8.9 |
| Zr.PV(POH).Pt.Pd-093 | 56 | 1 | 4.2 |
| | | 7 | 7.7 |
| Zr.PV(POH).Pt.Pd-32 | 31 | 1 | 2.5 |
| | | 23 | 4.9 |
| | | 27.5 | 5.1 |
| | | 30 | 5.2 |
| Zr.PV(POH).Pt.Pd-58 | 30 | 1 | 2.2 |
| | | 23 | 3 |
| | | 27.5 | 2.9 |
| | | 30 | 2.9 |

Zr*PV(POH) = $Zr(O_3POH)$ $(O_3PCH_2CH_2bipyridiniumCH_2CH_2PO_3)Cl$
Pd-Pt-# refers to Pt/(Pt + Pd) (wt./wt.)

TABLE 8

Altering pH with HCl, $H_2:O_2$ = 1:5, 1 atm using $Zr(O_3POH)$ $(O_3PCH_2CH_2bipyridiniumCH_2CH_2PO_3)Cl.Pt.Pd-093$.

| pH | Quantity of Cmpd. (mg) | Time (hrs.) | $H_2O_2$ (mM) | Turnover # (total) |
|---|---|---|---|---|
| 1 | 23 | 1.3 | 33 | 29 |
| | | 2.3 | 51 | |
| | | 4.6 | 71 | |
| | | 6.3 | 79 | |
| | | 8.3 | 80 | |
| | | 24 | 140 | |
| 2 | 22 | 1.3 | 18 | 17 |
| | | 3.3 | 68 | |
| | | 4.8 | 78 | |
| | | 5.8 | 80 | |
| | | 6.8 | 89 | |
| 3 | 23 | 1.0 | 17 | 16 |
| | | 2.8 | 23 | |
| | | 4.0 | 23 | |
| | | 6.3 | 19 | |

The above experiments all involved atmospheric pressure reactions. Two parameters are important in this regard, those are the initial rate of hydrogen peroxide formation and the steady state concentration of hydrogen peroxide. The steady state concentration indicates the concentration at which our system is making water from peroxide at the same rate that peroxide is being formed, while the initial rate is an indication of the rate of hydrogen peroxide formation. As can be seen in Table 5 our best steady state value is 140 mM. At steady state the rate of oxygen reduction (equation 1) and hydrogen peroxide reduction (equation 2) are equal, so that the concentration of hydrogen peroxide is constant. The initial rate of the reaction in these experiments is 30 turnovers per hour (based on the moles of viologen present in the system). These experiments were carried out with a catalyst which has an R of 0.093 and a mixture of 1:5 of $H_2:O_2$. The best DuPont catalyst (DU-D) treated in an identical manner produced only 77 mM hydrogen peroxide at steady state.

Other catalysts loose a good fraction of their activity very quickly. To test this we took one sample of the catalyst and used it in several successive experiments. The results are shown in Table 8. To minimize hazards, a mixture of hydrogen and air was used in these experiments, so that the steady state values for the peroxide concentration are low relative to the numbers quoted above. The first three experiments show very similar level of peroxide production. The fourth experiment, shows a lower level of activity than the first three. This level of activity is still much higher than that observed for the DuPont catalyst under identical conditions. Elemental analysis shows that after the fourth cycle the weight % of Pt and Pd have gone up slightly, while the amount of Zr has gone down. This observation suggests that the decrease in activity has to do with partial dissolution of the metal phosphonate.

EXAMPLE 31

High Pressure Hydrogen Peroxide Formation:

A number of experiments were performed with various combinations of gas pressures ($H_2$, $O_2$, $N_2$) in a 70 ml pressure vessel. Five mls of 0.1M HCl and 25 milligrams of $Zr(O_3POH)(O_3PCH_2CH_2bipyridiniumCH_2CH_2PO_3)Cl*Pt*Pd$ were added to the vessel. A mixture of oxygen, hydrogen, and nitrogen at the prescribed pressures was added to the vessel. The reactions were allowed to proceed for the specified times. Table 9 shows results for different gas pressures. The $H_2O_2$ concentrations are similar to those obtained in experiments at atmospheric pressure (see above). The data shows that an increase in either reactor vessel volume or an increase in pressure would yield higher $H_2O_2$ concentrations, i.e., if $P_{H2}$ and $P_{O2}$ were increased by a factor of 5 the results would be one molar $H_2O_2$ (using ex. 2 in Table 9).

TABLE 9

| Time (hrs) | \|$H_2O_2$\| final (moles/L) | Total pressure (psi) | $P_{O2}$ (psi) | $P_{H2}$ (psi) | $P_{N2}$ (psi) | Moles $H_2$ in system | Yield of $H_2O_2$ relative to $H_2$ in system |
|---|---|---|---|---|---|---|---|
| 15 | 0.143 | 175 | 100 | 15 | 60 | 0.0029 | 25% |
| 23 | 0.214 | 175 | 100 | 15 | 60 | 0.0029 | 37% |
| 48† | 0.410 | 175 | 100 | 15 | 60 | | |
| 18 | 0.084 | 150 | 120 | 6 | 24 | 0.0011 | 38% |
| 13 | 0.062 | 150 | 120 | 6 | 24 | 0.0011 | 28% |

†After 24 hours the system was vented and a fresh charge of the same gas mixture was added, then allowed to react for another 24 hours.

What is claimed is:

1. A catalytic process for producing hydrogen peroxide from oxygen and hydrogen comprising the steps of:
   A) treating an aqueous suspension of heterogeneous catalyst with a source of oxygen and a source of hydrogen;
   B) separating the catalyst; and,
   C) isolating the produced hydrogen peroxide,
wherein said catalyst is a complex of the formula:

$$[[(Y^1O_3{-}Z{-}Y^2O_3) \cdot p(X^{2/p-})]_{1-n} (Y^3O_3R^3)_{2n} Me^2]*Pt*Pd$$

wherein
   each of $Y^1$, $Y^2$, and $Y^3$, independently of the other, is phosphorus or arsenic;
   Z is a divalent group which reversibly forms a stable reduced form, said group containing two conjugated cationic centers which together have a negative $E°_{red}$ value;
   $Me^2$ is a trivalent or tetravalent metal of Group III, IVA, or IVB having an atomic number of at least 21 or a lanthanide;
   X is anion;
   n has a value of from 0 to 0.8; and
   p has a value of 1, 2 or 3; and
   $R^3$ is a nonreducible capping group.

2. A process according to claim 1 wherein Z is

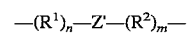

in which
   Z' is a divalent aromatic group containing at least two conjugated tetravalent nitrogen atoms;
   each of n and m, independently of the other, has a value of 0 or 1; and
   each of $R^1$ and $R^2$, independently of the other, is a divalent aliphatic or aromatic hydrocarbon group.

3. A process according to claim 2 wherein in Z', each tetravalent nitrogen atom is a ring member in separate aromatic ring systems which ring systems are joined to one another directly or through a conjugated hydrocarbon chain.

4. A process according to claim 3 wherein each aromatic ring system is a monocycle or fused polycycle comprising a pyridine, pyrazine, or pyrimidine ring each of which monocycle or fused polycycle is unsubstituted or substituted with alkyl of 1 to 6 carbon atoms.

5. A process according to claim 2 wherein in Z', both tetravalent nitrogen atoms are ring members in a fused polycyclic aromatic system.

6. A process according to claim 5 wherein the fused polycyclic aromatic system comprises two members independently selected from the group consisting of pyridine, pyrazine, and pyrimidine, said fused polycyclic aromatic system being unsubstituted or substituted with alkyl of 1 to 6 carbon atoms.

7. A process according to claim 2 wherein each of n and m is 1 and each of $R^1$ and $R^2$, independently of the other, is a straight or branched divalent alkane chain of six or less carbon atoms, an arene, or polyarene.

8. A process according to claim 1 wherein $Me^2$ is titanium, zirconium, hafnium, germanium, tin, or lead.

9. A process according to claim 8 wherein $Me^2$ is zirconium.

10. A process according to claim 1 wherein each of $Y^1$, $Y^2$, and $Y^3$ is phosphorus.

11. A process according to claim 1 wherein said catalyst is a complex of the formula:

$$SiO_2* [[(Y^1O_3{-}Z{-}Y^2O_3) \cdot p(X^{2/p-})]_{1-n} (Y^3O_3R^3)_{2n}Me^2]*Pt*Pd$$

wherein
   each of $Y^1$, $Y^2$, and $Y^3$, independently of the other, is phosphorus or arsenic;
   Z is a divalent group which reversibly forms a stable reduced form, said group containing two conjugated cationic centers which together have a negative $E°_{red}$ value;
   $Me^2$ is a trivalent or tetravalent metal of Group III, IVA, or IVB having an atomic number of at least 21 or a lanthanide;
   X is anion;
   n has a value of from 0 to 0.8; and
   p has a value of 1, 2 or 3; and
   $R^3$ is a nonreducible capping group.

12. A process according to claim 11 wherein Z is

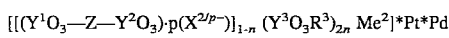

in which
   Z' is a divalent aromatic group containing at least two conjugated tetravalent nitrogen atoms;
   each of n and m, independently of the other, has a value of 0 or 1; and each of $R^1$ and $R^2$, independently of the other, is a divalent aliphatic or aromatic hydrocarbon group.

13. A process according to claim 12 wherein in Z', each tetravalent nitrogen atom is a ring member in separate aromatic ring systems which ring systems are joined to one another directly or through a conjugated hydrocarbon chain.

14. A process according to claim 13 wherein each aromatic ring system is a monocycle or fused polycycle comprising a pyridine, pyrazine, or pyrimidine ring each of which monocycle or fused polycycle is unsubstituted or substituted with alkyl of 1 to 6 carbon atoms.

15. A process according to claim 12 wherein in Z', both tetravalent nitrogen atoms are ring members in a fused polycyclic aromatic system.

16. A process according to claim 15 wherein the fused polycyclic aromatic system comprises two members independently selected from the group consisting of pyridine, pyrazine, and pyrimidine, said fused polycyclic aromatic system being unsubstituted or substituted with alkyl of 1 to 6 carbon atoms.

17. A process according to claim 12 wherein each of n and m is 1 and each of $R^1$ and $R^2$, independently of the other, is a straight or branched divalent alkane chain of six or less carbon atoms, an arene or polyarene.

18. A process according to claim 11 wherein $Me^2$ is titanium, zirconium, hafnium, germanium, tin, or lead.

19. A process according to claim 18 wherein each of $Me^2$ is zirconium.

20. A process according to claim 11 wherein each of $Y^1$, $Y^2$, and $Y^3$ is phosphorus.

* * * * *